United States Patent
Driemel

(10) Patent No.: US 9,138,164 B2
(45) Date of Patent: Sep. 22, 2015

(54) DIRECT CONNECTION HEAD COIL HAVING HEIGHT ADJUSTMENT

(75) Inventor: Daniel Driemel, Oederan (DE)

(73) Assignee: Siemens Aktiengesellschaft, München (DE)

( * ) Notice: Subject to any disclaimer, the term of this patent is extended or adjusted under 35 U.S.C. 154(b) by 61 days.

(21) Appl. No.: 13/553,607

(22) Filed: Jul. 19, 2012

(65) Prior Publication Data

US 2013/0184563 A1 Jul. 18, 2013

(30) Foreign Application Priority Data

Jul. 21, 2011 (DE) .......... 10 2011 079 565

(51) Int. Cl.
| | |
|---|---|
| *A61B 5/05* | (2006.01) |
| *A61B 5/055* | (2006.01) |
| *G01R 33/34* | (2006.01) |
| *G01R 33/3415* | (2006.01) |
| *G01R 33/36* | (2006.01) |

(52) U.S. Cl.
CPC ........ A61B 5/0555 (2013.01); G01R 33/34007 (2013.01); G01R 33/3415 (2013.01); G01R 33/34084 (2013.01); G01R 33/36 (2013.01)

(58) Field of Classification Search
CPC ........... A61B 5/0555; G01R 33/34007; G01R 33/34084; G01R 33/3415; G01R 33/36
USPC ............................ 600/407–430; 324/318–322
See application file for complete search history.

(56) References Cited

U.S. PATENT DOCUMENTS

| | | | |
|---|---|---|---|
| 6,943,551 B2 | 9/2005 | Eberler et al. | |
| 7,489,133 B1 | 2/2009 | Keidl et al. | |
| 8,099,150 B2* | 1/2012 | Piferi et al. | 600/422 |
| 2009/0021255 A1* | 1/2009 | DeVries et al. | 324/318 |
| 2009/0079431 A1* | 3/2009 | Piferi et al. | 324/318 |
| 2009/0088627 A1* | 4/2009 | Piferi et al. | 600/422 |
| 2009/0306494 A1* | 12/2009 | Scarth et al. | 600/411 |
| 2009/0306495 A1* | 12/2009 | Scarth et al. | 600/415 |
| 2010/0185198 A1* | 7/2010 | Piferi et al. | 606/54 |
| 2010/0280361 A1* | 11/2010 | DeVries et al. | 600/422 |
| 2011/0040174 A1 | 2/2011 | Driemel | |
| 2011/0279119 A1* | 11/2011 | Driemel et al. | 324/318 |
| 2012/0126814 A1* | 5/2012 | Fischer et al. | 324/318 |
| 2012/0136239 A1* | 5/2012 | Scarth et al. | 600/411 |
| 2013/0076358 A1* | 3/2013 | Taracila et al. | 324/322 |
| 2013/0131498 A1* | 5/2013 | Taracila et al. | 600/422 |

FOREIGN PATENT DOCUMENTS

| | | |
|---|---|---|
| DE | 103 14 215 B4 | 11/2006 |
| DE | 10 2009 036 939 A1 | 2/2011 |

OTHER PUBLICATIONS

German Office Action dated Apr. 24, 2012 for corresponding German Patent Application No. DE 10 2011 079 565.0 with English translation.

* cited by examiner

*Primary Examiner* — Sanjay Cattungal
(74) *Attorney, Agent, or Firm* — Lempia Summerfield Katz LLC

(57) ABSTRACT

A head coil for a magnetic resonance tomography device includes a lower part and an upper part that may be positioned above the lower part. The lower part has a lower part base that may be placed on a patient couch for the magnetic resonance tomography device and a lower part resting part that is moveable relative to the lower part base.

26 Claims, 8 Drawing Sheets

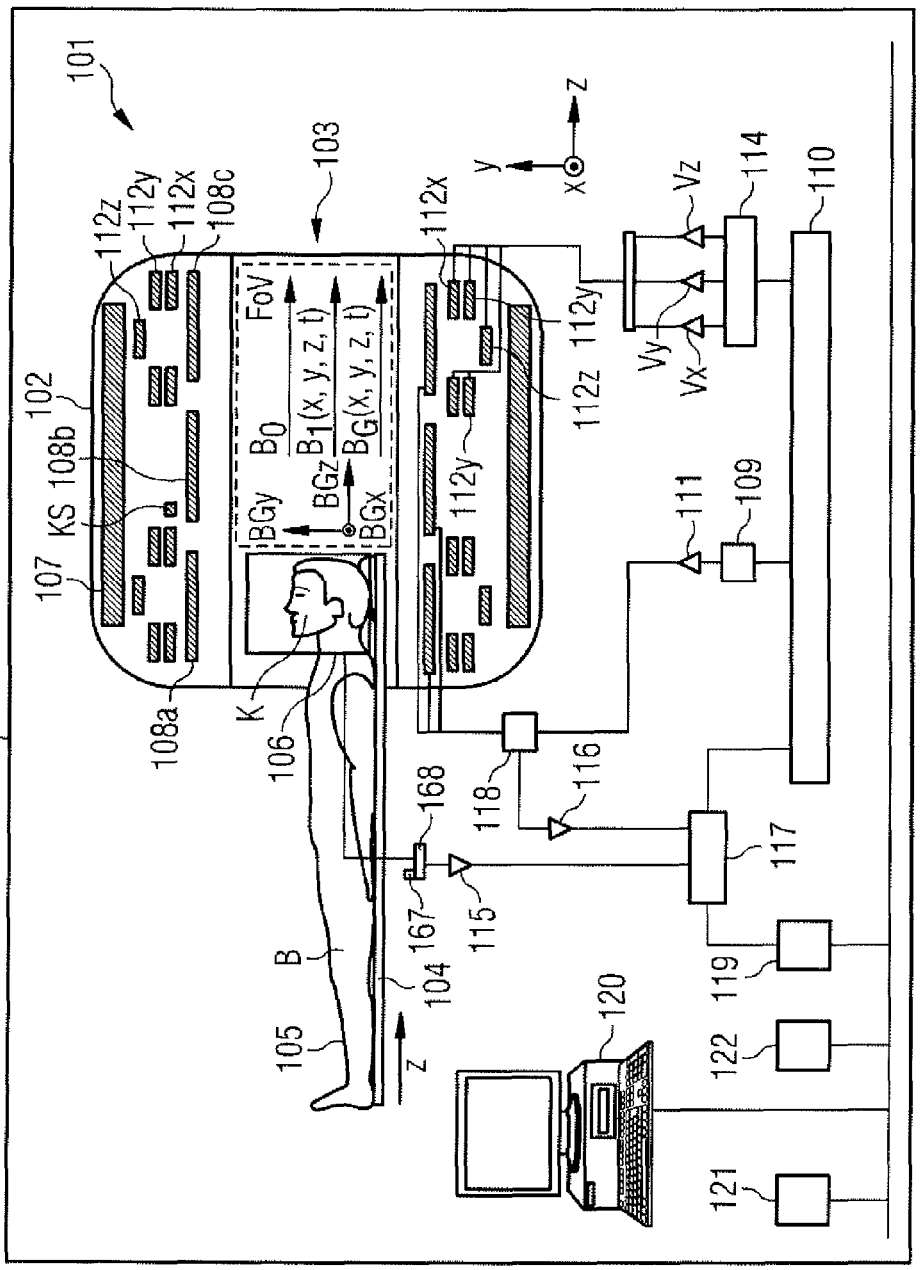

DIRECT CONNECTION HEAD COIL HAVING HEIGHT ADJUSTMENT

This application claims the benefit of DE 10 2011 079 565.0, filed on Jul. 21, 2011.

BACKGROUND

The present embodiments relate to a head coil for a magnetic resonance tomography (MRT) system.

Magnetic resonance tomography devices for examining objects or patients using magnetic resonance tomography (MRT, MRI) are described, for example, in DE 10314215B4.

In MR tomography, images with a high signal-to-noise ratio (SNR) may be recorded with local coils. The local coils are antenna systems that are attached in the immediate vicinity of (anterior) or below (posterior) the patient. During an MR measurement, the excited cores induce a voltage into the individual antennae of the local coil. The induced voltage is amplified with a low noise preamplifier (LNA, preamp) and is forwarded over a cable to receive electronics. In order to improve the SNR in, for example, highly resolved images, high field systems are used (e.g., 1.5 T to 12 T and more). Since more individual antennae may be connected to an MR receiving system than there are receivers present, a switching matrix (e.g., RCCS) is integrated between receiving antenna and receiver. This routes the currently active receiving channels (e.g., the receiving channels lying precisely within the field of view of the magnet) to the existing receiver. More coil elements than there are receivers present may thus be connected, since with a whole body coverage, only the coils that are in the field of view (FoV) and/or in a homogeneity volume of the magnet have to be read out.

For example, an antenna system that may include one or several antenna elements or coil elements (e.g., an array coil) is referred to below as "coil" (e.g., a local coil). The individual antenna elements are, for example, embodied as loop antennae (e.g., loops), butterfly coils or saddle coils. A coil includes the coil elements, a preamplifier, further electronics (e.g., cable traps), cabling, a housing and may include a cable with a plug, by which the coil is connected to the MRT system. The receiver (RX) attached on the system side filters and digitizes the signal received by the local coil and transfers the data to the digital signal processing. The digital signal processing may derive an image or a spectrum from the measurement and provides the image or spectrum to the user for diagnosis.

In order to position patients with abnormal changes to the cervical spine (e.g., Bechterew, torticollis, hyperkyphosis or accident patients in the head coils), the head coil may be raised in the rear head area, since the patient is not in the position to lie his/her head flat in the coil. Contacting systems use a defined assignment between the patient couch and the head coil, for example, with direct contacting of the head coil into the patient couch or with alternative contacting variants, such as capacitive coupling between the patient couch and the head coil. With contacting systems, a movement of the coil relative to the patient couch in an inserted plugged-in state may not be possible. The coil and the patient couch form a fixed plug-in unit.

For coils that are in direct contact with the patient couch (e.g., the Siemens head coil for the Aera and Skyra systems), or for alternative contacting possibilities with a fixed assignment between the patient couch and the coil, a movement of the coil relative to the patient couch may be enabled for Bechterew patients, for example. Higher positioning of the pelvis is, for example, achieved by transferring the patient with suitable positioning materials. Head coils with a correspondingly long external connecting line are rotated about a center of rotation that is located below the neck region of the patient. This results in a tilting movement of the coil. A further alternative solution is the underlaying of wedge-shaped parts below the head coil.

SUMMARY AND DESCRIPTION

The present embodiments may obviate one or more of the drawbacks or limitation in the related art. For example, a local coil for a magnetic resonance tomography device may be further optimized.

In one embodiment, an angular adjustment about a fixed center of rotation (e.g., tilting of the coil) is provided.

In another embodiment, an angular adjustment with a displaceable center of rotation is provided, and tilting and displacement of a moveable part of the head coil is enabled. This achieves a maximally useable couch length and a position of the head in the z-direction.

In one embodiment, a height adjustment of the head coil is provided. The design of a curved path of the moveable part of the head coil relative to a base of the head coil provides for different rising gradients in the movement of the moveable part of the head coil (e.g., starting flat and rising more steeply).

A screw-type gearing for driving the movement enables the position to be fixed on account of self-locking. Separation of a contact part (e.g., in the base of the head coil) and an antenna part (e.g., in the moveable part of the head coil) within the head coil may be provided. Flexible line connections may provide movability of the moveable part including a rest for a head (i.e., lower part headrest, lower part headrest part, or lower part head support) of the lower part of the head coil relative to the lower part base.

BRIEF DESCRIPTION OF THE DRAWINGS

FIG. 8 shows a schematic and simplified representation of an MRT system.

DETAILED DESCRIPTION OF THE DRAWINGS

Figure 1:
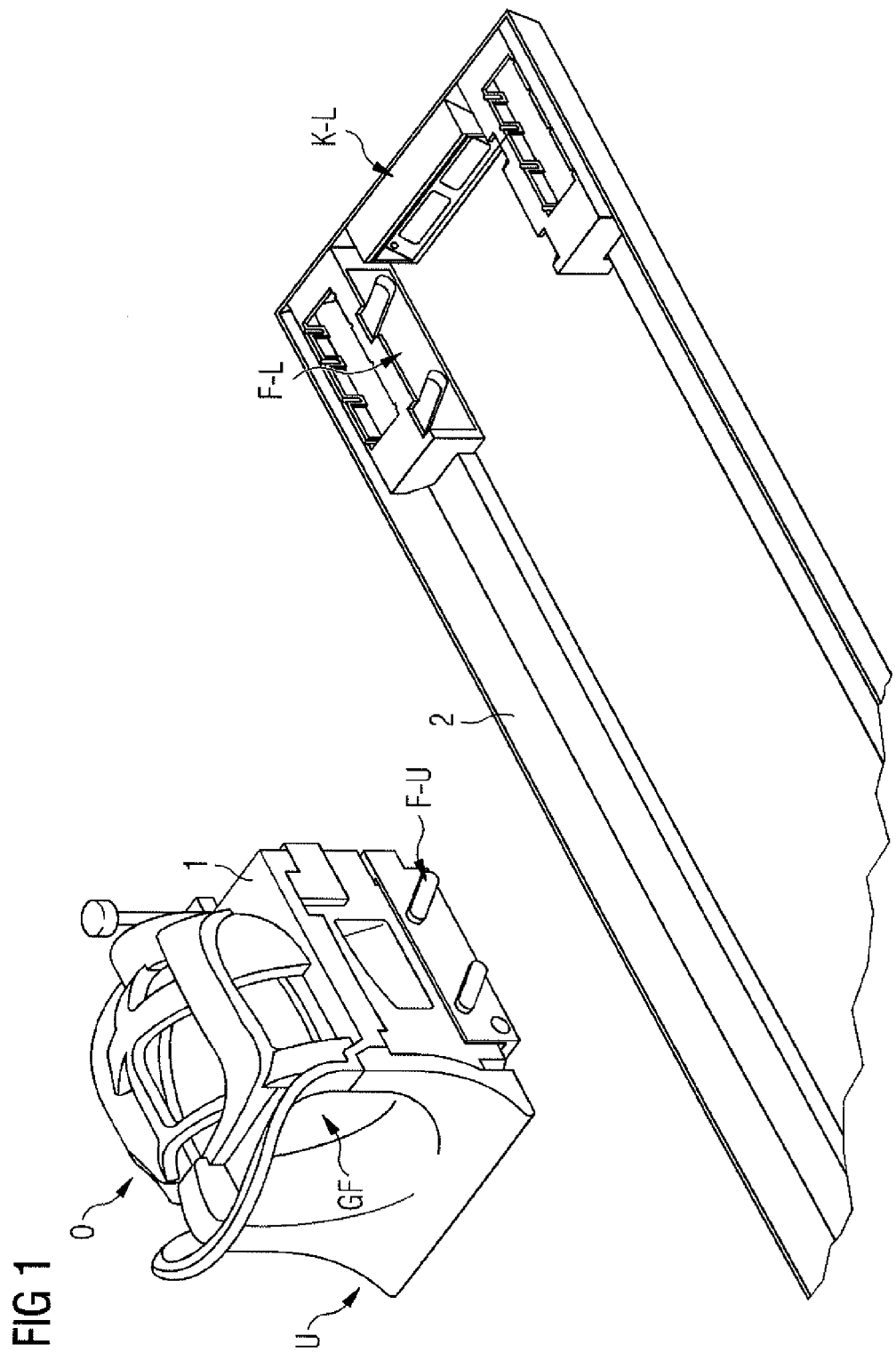
FIG. 1 shows a perspective view of one embodiment of a head coil and a detail of a patient couch with a guide for the head coil and a connecting strip for connection of the head coil to the patient couch.

FIG. 8 shows a magnetic resonance tomography (MRT) device 101 (e.g., an MRT imaging device) in a shielded room or Faraday cage F having a whole body coil 102 with a tubular space 103, into which a patient couch 104 with a body 105 (e.g., an examination object such as a patient; with or without local coil arrangement 106) may be moved in the direction of arrow z in order to generate recordings of the patient 105 using an imaging method. The local coil arrangement 106 (e.g., fastened with the same or a further belt) is arranged on the patient (e.g., fastened with a belt). Recordings of a sub-area of the body 105 in a field of view (FOV) may be generated with the local coil arrangement 106 in a local area (e.g., the FOV) of the MRT device 101. Signals of the local coil arrangement 106 may be evaluated by an evaluation device or facility (e.g., including elements 168, 115, 117, 119, 120, 121) of the MRT device 101 (e.g., converted into images, stored or displayed) by way of coaxial cables or by radio (e.g., element 167), which may be connected to the local coil arrangement 106, for example.

In order to examine the body 105 (e.g., the examination object or the patient) by magnetic resonance imaging using the MRT device 101, different magnetic fields that are attuned to one another as precisely as possible in terms of spatial and temporal characteristics, are irradiated onto the body 105. A strong magnet (e.g., a cryomagnet 107) in a measuring cabin with a tunnel-shaped opening 103, for example, generates a strong static main magnetic field $B_0$ that amounts, for example, to between 0.2 tesla to 3 tesla or more. The body 105 to be examined is moved into an approximately homogenous area of the main magnetic field $B_0$ in the FoV when positioned on a patient couch 104. Excitation of the nuclear spin of atomic nuclei of the body 105 takes place by way of magnetic high-frequency excitation pulses B1 (x, y, z, t) that are irradiated by way of a high frequency antenna (and/or if necessary, a local coil arrangement) that is shown in FIG. 8 in simplified form as a body coil 108 (e.g., a multipart body coil 108a, 108b, 108c). High frequency excitation pulses are, for example, generated by a pulse generation unit 109 that is controlled by a pulse sequence control unit 110. After amplification using a high frequency amplifier 111, the high frequency excitation pulses are routed to the high frequency antenna 108. The high frequency system shown in FIG. 8 is only shown schematically. In other embodiments, more than one pulse generation unit 109, more than one high frequency amplifier 111, and several high frequency antennae 108 a, b, c are used in a magnetic resonance device.

The MRT device 101 has gradient coils 112x, 112y, 112z, with which during measurement, magnetic gradient fields are irradiated for selective layer excitation and for local encoding of the measurement signal. The gradient coils 112x, 112y, 112z are controlled by a gradient coil control unit 1104 that, similarly to the pulse generation unit 109, is connected to the pulse sequence control unit 110.

Signals emitted by the excited nuclear spin (e.g., the atom nucleus in the examination object) are received by the body coil 108 and/or at least one local coil arrangement 106, amplified by an assigned high frequency preamplifier 116 and further processed and digitized by a receiving unit 117. The recorded measurement data is digitized and stored as complex numerical values in a k-space matrix. An associated MR image may be reconstructed from values populating the k-space matrix using a multidimensional Fourier transformation.

For a coil that may be operated both in transmit and also in receive mode (e.g., the body coil 108 or a local coil 106), the correct signal forwarding is controlled by an upstream transmit-receive switch 118.

An image processing unit 119 generates an image from the measurement data, which is displayed to a user by way of a control console 120 and/or is stored in a storage unit 121. A central computing unit 122 controls the individual system components.

In MR tomography, images with a high signal-to-noise ratio (SNR) may be recorded with local coil arrangements. The local coil arrangements are antenna systems that are attached in the immediate vicinity of (anterior), below (posterior), on, or in the body. With an MR measurement, the excited cores induce a voltage in the individual antennae of the local coil. The induced voltage is amplified with a low noise preamplifier (e.g., LNA, Preamp) and is routed to the receive electronics. In order to improve the signal-to-noise ratio with high resolution images, high field systems are used (e.g., 1.5 T and more).

If more individual antennae may be connected to an MR receiver system than there are receivers present, a switching matrix (e.g., an RCCS) is integrated between the receiving antennae and the receiver, for example. This routes the currently active receiving channels (e.g., the receiving channels that lie precisely in the FoV of the magnet) to the existing receiver. As a result, more coil elements than there are receivers present may be connected, since with a whole body coverage, only the coils that are in the FoV and/or in the homogeneity volume of the magnet are read out.

An antenna system may be referred to as a local coil arrangement 106, for example, which may include, for example, one or several (e.g., an array coil) antenna elements (e.g., coil elements). The individual antenna elements are embodied, for example, as loop antennae (e.g., loops), butterfly, flexible coils or saddle coils. A local coil arrangement includes, for example, coil elements, a preamplifier, further electronics (e.g., a cable trap), a housing, rests and may include a cable with a plug, by which the local coil arrangement is connected to the MRT system. A receiver 168 attached to the system side filters and digitizes a signal received from a local coil 106 (e.g., by radio) and transfers the data to a digital signal processing facility. The digital signal processing facility may derive an image or a spectrum from the data obtained by a measurement and may make the image or the spectrum available to the user, for example, for subsequent diagnosis by the user and/or storage.

Exemplary embodiments of MRT head local coils 106 are described in more detail with the aid of FIGS. 1-7.

A patient 105 is to be examined while resting on a patient couch 104 in an MRT device 101 using a magnetic resonance tomography device head coil as a local coil 106 on his/her head K.

Embodiments of a directly contacted head coil 1 (e.g., plugged into a power supply and/or data connections (K-L) in a patient couch such as in FIG. 1) into an MRT controller (e.g., including elements 110, 117) are described. The head coils 1 enable a movement of a head K of a patient relative to a patient couch 2 for the MRT device 101 on account of the structural design. In the embodiments of the head coil 1 shown, the head K of a patient may be moved from a lower position relative to the patient couch 2, as in FIG. 2 or FIG. 4, into a high position relative to the patient couch 2, as in FIG. 4 or FIG. 5, and fixed there.

A moveable coil housing U, 3 and 4 of the coil lower part U of the local coil 106, is divided (e.g., into two components 3, 4) and has a flexible electrical connection 5 (e.g., inserted, direct) between a contact plug K-U of the local coil 106 on a side in the direction of the patient couch 104 and therefore from the patient couch 104 to electrical components (not shown) (e.g., a controller, an amplifier, a filter) of antenna elements (e.g., individual coils) in the local coil 106. The coil lower part U includes moveable parts 3, 4 and/or parts that may be moved relative to one another. The moveable part 3 is also referred to as a lower part headrest part 3 with, for example, a lower part head support resting surface GF for the head K and, if necessary, a lower part cladding. The moveable part 4 is also referred to as a lower part base 4 including, for example, a contact and a guide part.

The lower part headrest part 3 is part of the lower part U, upon which the head K may rest (e.g., on the lower part head support resting surface GF).

The electrical connection 5 emerges (e.g., as a line to connection K-U) from the lower part head support 3 through a housing opening. A path of the lifting movement of the head K (e.g., from a low position into a high position) defines the length of the electrical connection.

Three exemplary embodiments are described below in order to raise and/or lower (e.g., height adjustment of the resting surface GF for the head K relative to the patient couch 104) the head coil 106, which is directly contacted (e.g., by inserting the connection K-U with the connection K-L into one another).

Figure 2:
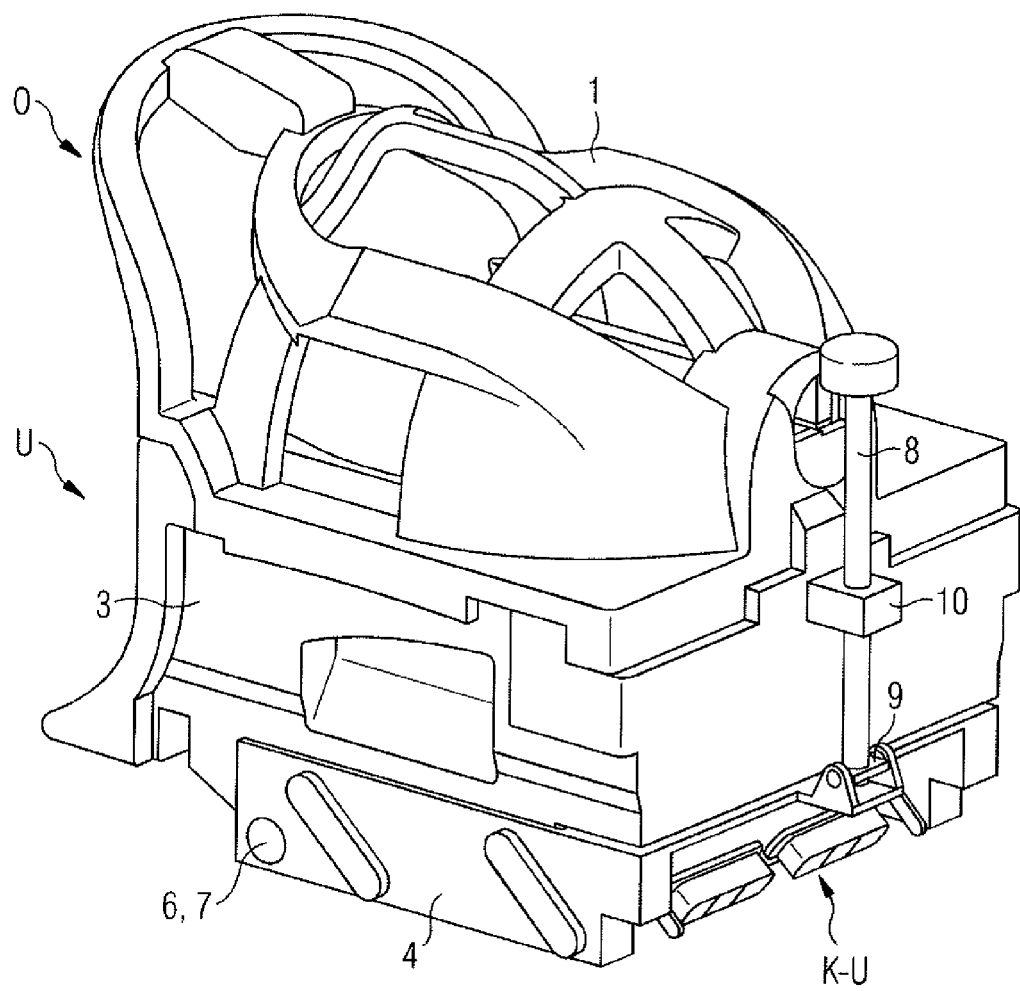
FIG. 2 shows a perspective view of one embodiment of a head coil with components of a lower part of the head coil that are pivotable relative to one another for the head-height adjustment in a lower position for the head.
Figure 3:
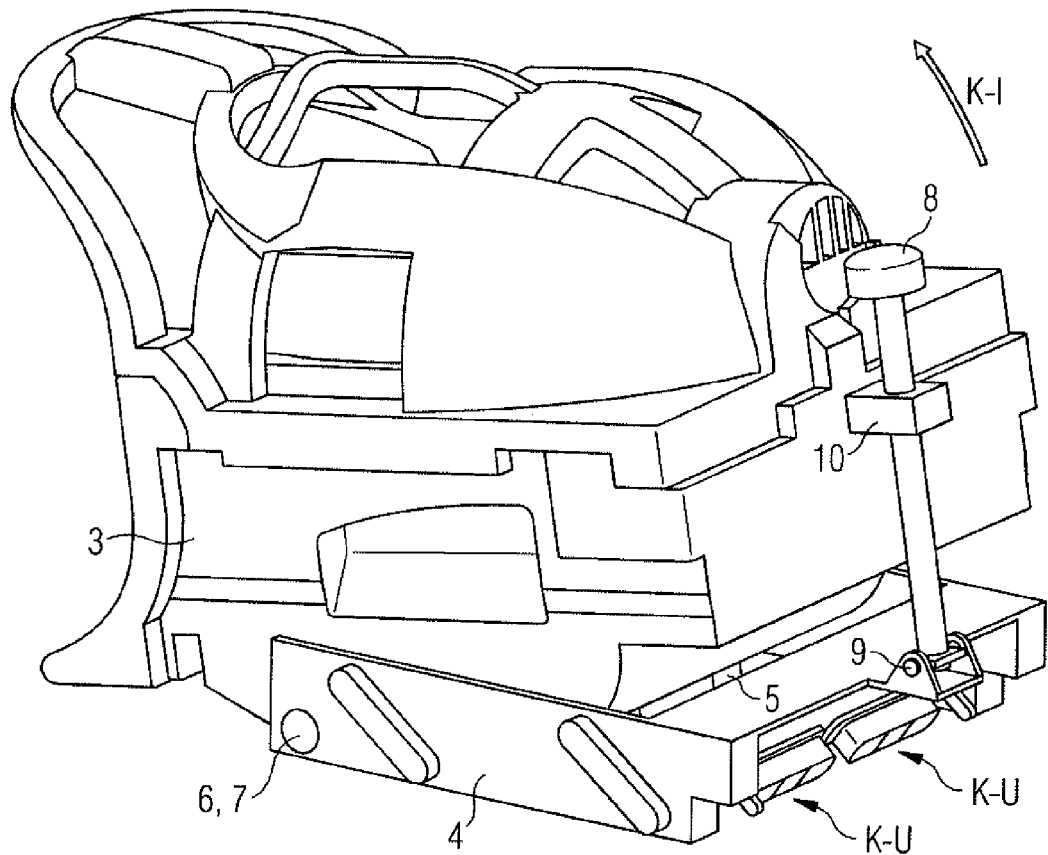
FIG. 3 shows a perspective view of one embodiment of a head coil having components of the lower part of the head coil that are pivotable relative to each other for head-height adjustment and displaced in a higher position for the head.

In one embodiment according to FIGS. 2-3, a tilting of the lower part head support 3 and thus of the resting surface GF of the head coil 106 is produced about a center of rotation 6 (e.g., without direct contacting). A variable angular adjustment of, for example, 0-45 degrees of the head resting surface GF of the head coil 106 relative to the patient couch 104 and/or horizontal plane x-z, for example, is enabled.

An inner area of the head coil 1 moves in the direction x (e.g., head-foot direction) towards the feet of the patient.

Points of rotation 6 on both sides are bearings (e.g., ball-bearings, roller bearings, recesses) in the lower part base 4. A moveable axle 7 such as, for example, bolts engage the bearings 6 on the lower part headrest 3. The axles 7 are pressed outwards, for example, by pressure springs (not shown). The pressure springs are pushed inwards for assembly of the lower part head support 3 into the lower part base 4.

A screw-type gearing, for example, realizes the height adjustment of the lower part head support 3 (e.g., without or together with the upper part O placed upon the lower part head support 3). A spindle 8 has a tiltable swivel joint fastened to the lower part base 4. A nut 10, through which the spindle 8 passes, is fixedly connected to the lower part head support 3. By rotating the spindle 8, the lower part head support 3 of the head coil 1 is tilted around the center of rotation 6 relative to the lower part base 4 (arrow Ki).

Figure 4:
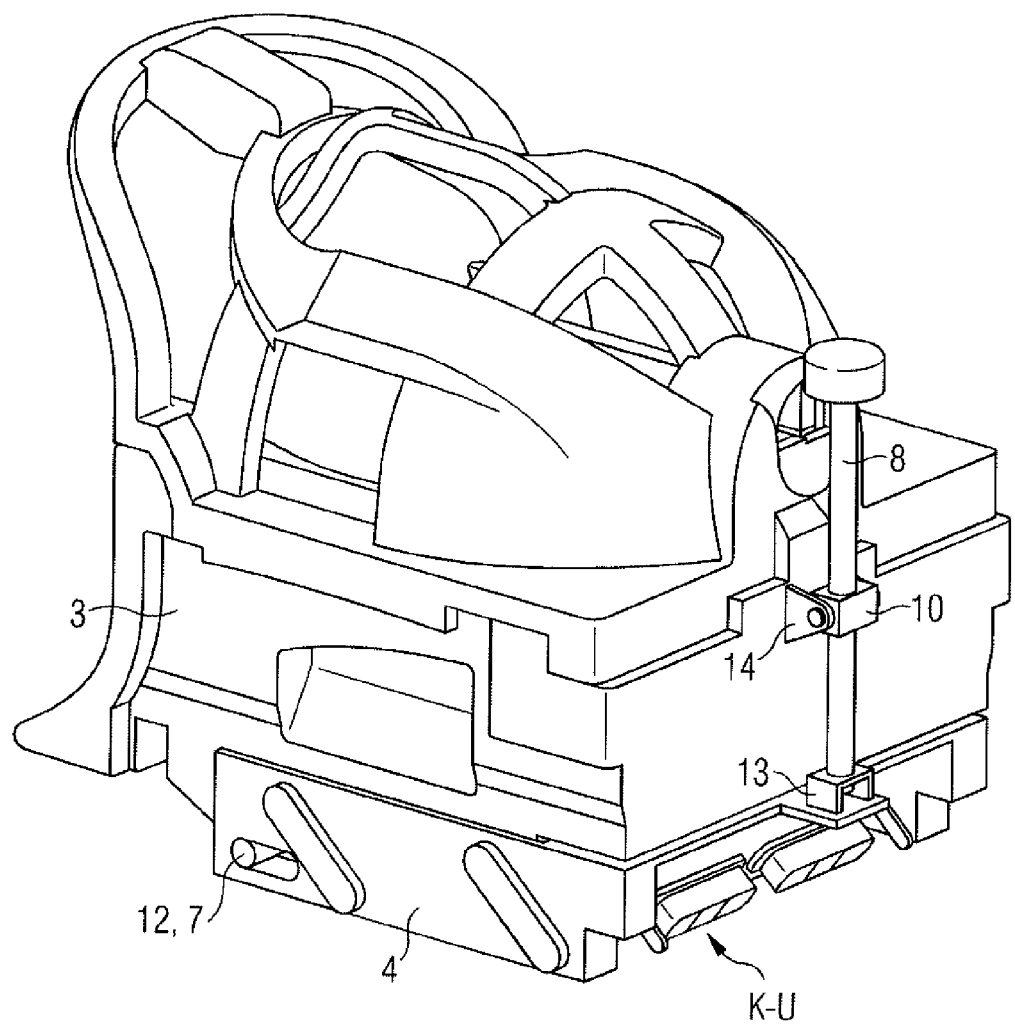
FIG. 4 shows a perspective view of one embodiment of a head coil having components of the lower part of the head coil that are pivotable relative to each other for head-height adjustment and displaced in a lower position for the head.
Figure 5:
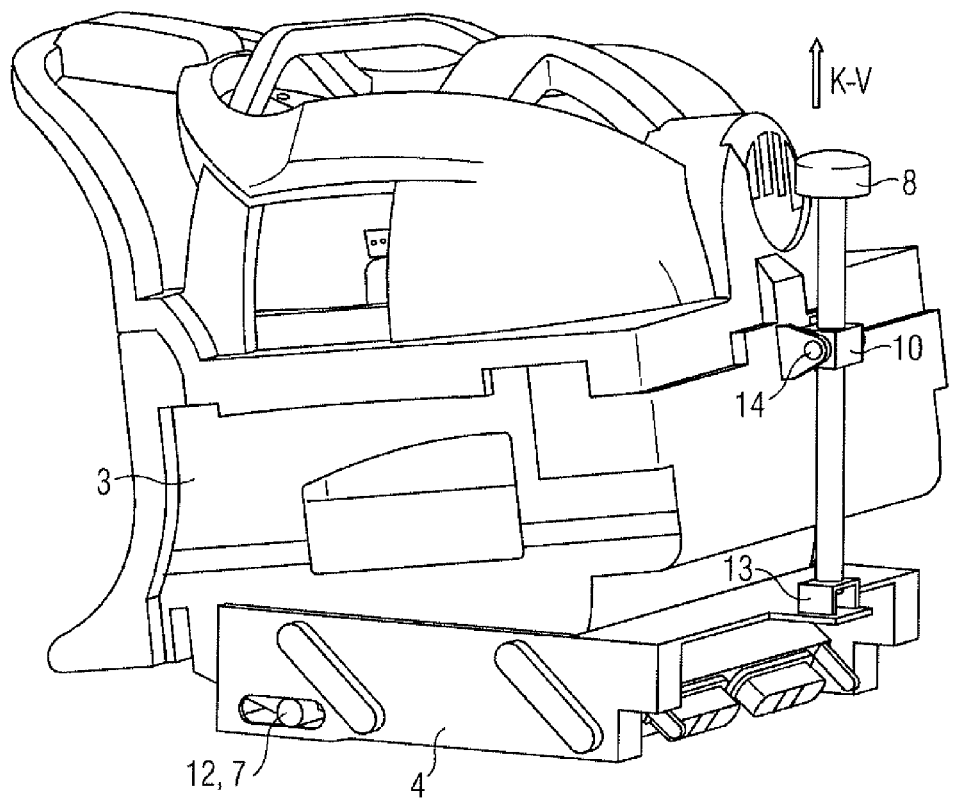
FIG. 5 shows a perspective view of one embodiment of a head coil having components of the lower part of the head coil that are pivotable relative to each other for head-height adjustment and displaced in a higher position for the head.
Figure 6:
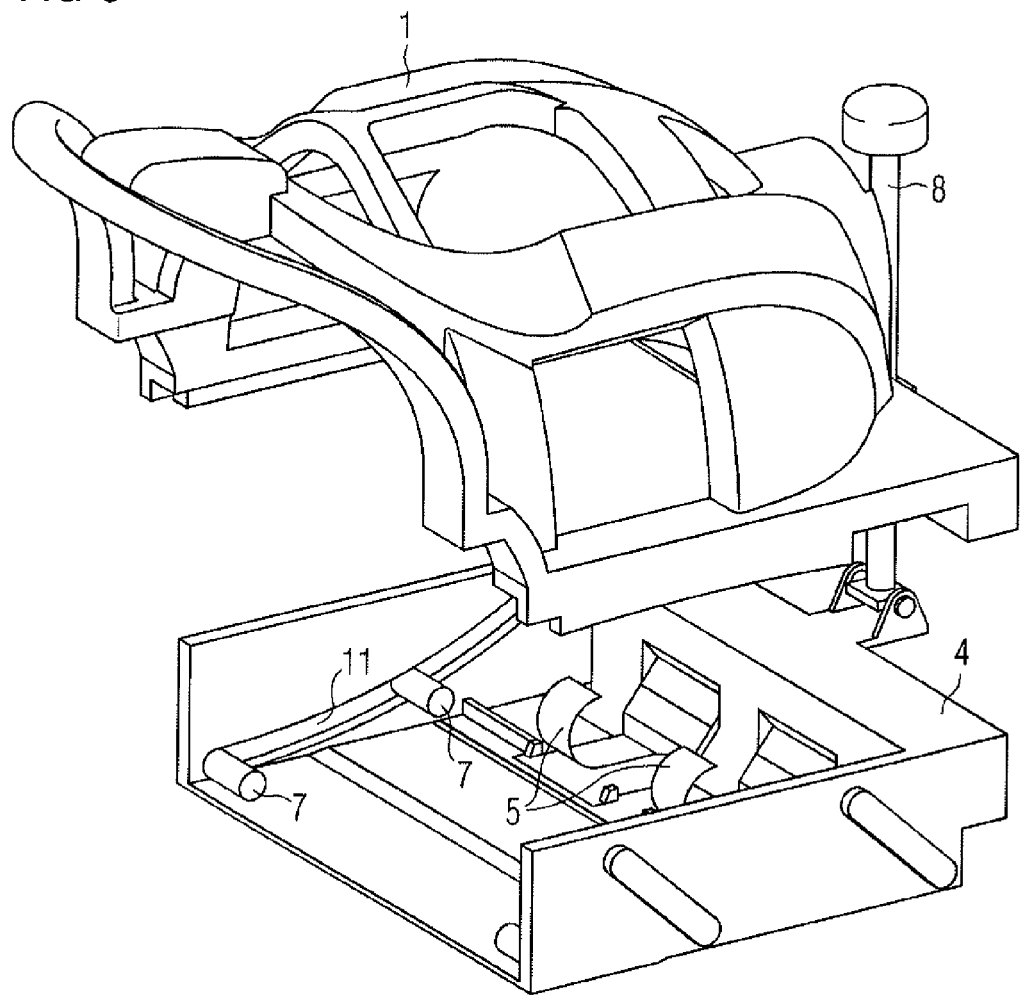
FIG. 6 shows a perspective view of one embodiment of a base of the lower part and the upper part of a head coil having components of the lower part that are displaceable relative to one another in a guide for head-height adjustment.
Figure 7:
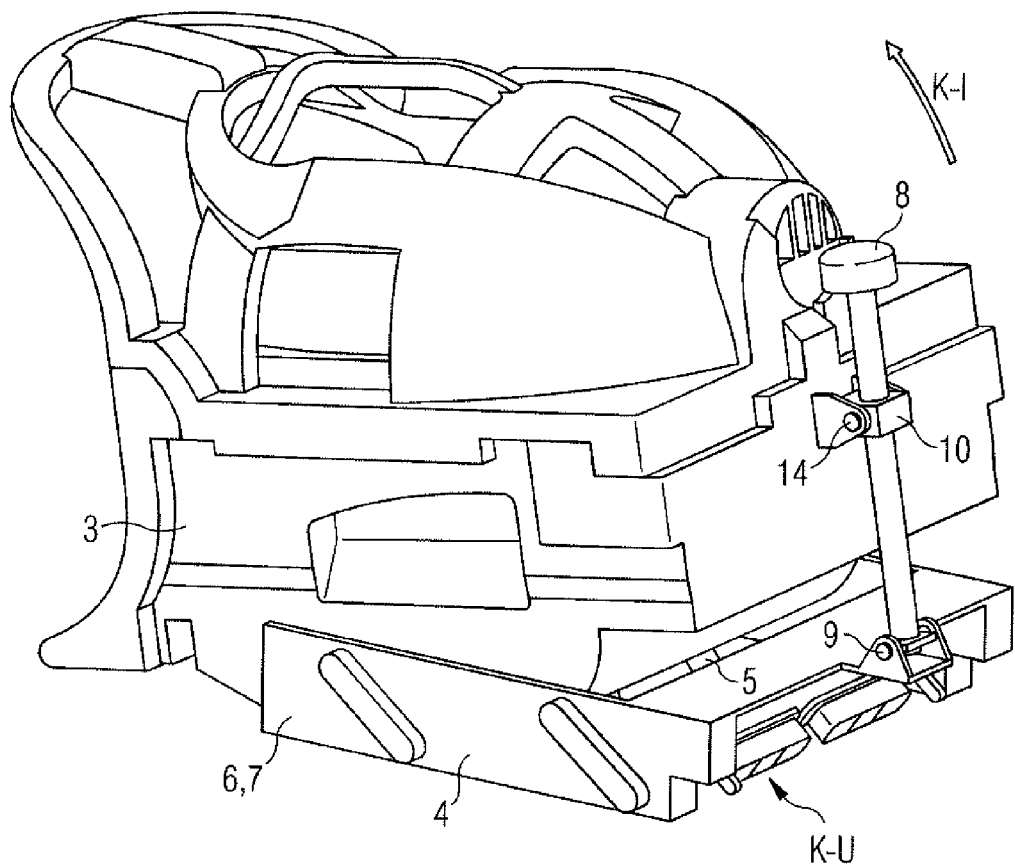
FIG. 7 shows a perspective view of one embodiment of a head coil having components of the lower part of the head coil that are moveable relative to one another in a guide for head-height adjustment in a higher position for the head.

Another embodiment, according to FIGS. 4-5, has no fixed point of rotation, but instead a prismatic joint 12. An inner part (e.g., the lower part headrest part 3) of the head coil 106 only moves upwards (e.g., in the y direction) in a linear movement. As a result, the center of rotation of the moveable lower part headrest part 3 of the coil is drawn upwards in the y-direction. The position of the head remains approximately or very precisely constant in the z direction. The position of the head is only placed in a higher position. This is advantageous for a "PUSH BUTTON" use and/or permanently programmed couch displacement. By rotating the spindle 8, which is fastened to the lower part base 4 in a rotary hinge 13, in which no tilting is, for example, provided and a spindle remains vertical, the nut 10 moves linearly along the spindle 8 (e.g., arrow Kv in direction y). The axle 7 is rotated and, at the same time, moved linearly in the prismatic joint 12. In this embodiment, the nut 10 may have a swivel joint 14 on the lower part head support 3. An embodiment, according to FIGS. 6-7, moves the directly contacted head coil 1 (e.g., by plugging into connections in the patient couch) on a curved path 11 in the divided housing of the coil lower part relative to the patient couch 104. The curved path may realize different rising gradients of the lifting movement of the inner lower part head support part 3 in the lower part base 4 of the head coil 1.

Four pressure-sprung axles 7, for example, engage with the curved path 11 on both sides. The screw-type gearing used for driving purposes includes, for example, moveable connections both for the spindle 8 (e.g., connected to a tiltable axis of rotation 9) and also for the nut 10 (e.g., connected to a swivel joint 14).

Several variants are provided for driving the movement of the head coil 1. Manual use of a screw-type gearing a toothed wheel/toothed bar, and/or a Bowden cable may be used. The head coil 1 may be self-locking and may not need to be clamped for position fixing purposes. When removing the head coil from the direct contacting, the self-locking of the height adjustment prevents a movement of the height adjustment that is determined by the pulling movement. With a divided sprung nut, the screw-type gearing is free of play, and the head coil is protected from vibrations in each position.

Embodiments allow for movement of a head coil that is in direct contact with the patient couch, relative to the patient couch in order to be able to ergonomically examine patients with, for example, a Bechterew disease, torticollis or accident patients in a more comfortable position. A divided coil lower part, including a lower part head support and lower part base, enables movement between the contact part and the remaining head coil.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A head coil for a magnetic resonance tomography device, the head coil comprising:
   a lower part of a head coil comprising:
      a lower part base that is placeable on a surface of a patient couch for the magnetic resonance tomography device; and
      a lower part headrest part that is moveable relative to the lower part base and moveable from a lower position closer to the surface of the patient couch to a higher position farther above the surface of the patient couch;
   an upper part of the head coil that is positionable above the lower part; and
   a toothed wheel, a toothed bar, a Bowden cable, a screw-type gearing, or a combination thereof for manual or motor-powered height adjustment of the lower part headrest part relative to the lower part base.

2. The head coil as claimed in claim 1, wherein the lower part base is pivotably moveable relative to the lower part headrest part.

3. The head coil as claimed in claim 2, wherein the lower part base is pivotably moveable relative to the lower part headrest part by axles that are pivotably arranged in a swivel joint.

4. The head coil as claimed in claim 1, wherein the lower part headrest part is displaceably moveable relative to the lower part base.

5. The head coil as claimed in claim 4, wherein the lower part headrest part is displaceably moveable relative to the lower part base by a prismatic joint of the lower part.

6. The head coil as claimed in claim 1, wherein the lower part headrest part is pivotably and displaceably moveable relative to the lower part base.

7. The head coil as claimed in claim 6, wherein the lower part headrest part is pivotably and displaceably moveable relative to the lower part base through axles that are arranged rotatably and displaceably in a prismatic joint.

8. The head coil as claimed in claim 1, wherein the upper part is positionable above the lower part by placement on the lower part.

9. The head coil as claimed in claim 8, wherein the upper part is positionable above the lower part by at least one surface, edge, point, or a combination thereof of the upper part resting on the lower part.

10. The head coil as claimed in claim 1, wherein the lower part base comprises at least one connection for contacting onto, insertion into, or contacting onto and insertion into a connection on the patient couch.

11. The head coil as claimed in claim 10, wherein the connection on the patient couch comprises a connection for supply voltage, data, or supply voltage and data.

12. The head coil as claimed in claim 1, wherein the lower part headrest part of the lower part comprises a lower part housing or part of a lower part housing.

13. The head coil as claimed in claim 1, wherein the lower part headrest part of the lower part comprises at least one housing resting surface, on which the head of a patient is restable, which forms a space with the upper part, into which the head of at least a majority of patients fits, or a combination thereof.

14. The head coil as claimed in claim 7, wherein the axles are pushed outwards by pressure springs and are pushable inwards into the lower part base in order to assemble the lower part headrest part.

15. The head coil as claimed in claim 1, wherein the screw-type gearing comprises a spindle comprising a swivel joint fastened to the lower part base, wherein the lower part headrest part is tiltable about a center of rotation relative to the lower part base by rotating the spindle.

16. The head coil as claimed in claim 15, further comprising a nut, through which the spindle runs, the nut being fixedly connected to the lower part headrest part.

17. The head coil as claimed in claim 1, further comprising a prismatic hinge by which the lower part headrest part and the lower part base are moveable in a linear movement relative to one another.

18. The head coil as claimed in claim 17, wherein the lower part headrest part and the lower part base are moveable in the linear movement relative to one another about a center of rotation in a region of the head coil that is provided for the position of a head in order to approximately or accurately keep the position of the head constant in a longitudinal direction of the patient couch and only move a height of the head above the patient couch.

19. The head coil as claimed in claim 1, wherein the screw-type gearing comprises a spindle rotatably fastened on the lower part base in a recess, wherein a nut is pivotably connected to the lower part headrest part in a hinge, the spindle operable to run rotatably in the nut.

20. The head coil as claimed in claim 19, further comprising tiltable connections.

21. The head coil as claimed in claim 20, wherein the tiltable connections comprise hinges for the spindle and the nut.

22. The head coil as claimed in claim 1, wherein the lower part base comprises guides that guide the lower part headrest part relative to the lower part base.

23. The head coil as claimed in claim 1, wherein the lower part base comprises guides that guide the lower part headrest part relative to the lower part base, a curve of the guides defining a rising gradient of movement of the lower part headrest part relative to the lower part base, in particular starting flat and rising more steeply.

24. The head coil as claimed in claim 23, wherein the rising gradient of movement starts flat and rises more steeply.

25. The head coil as claimed in claim 1, further comprising a self-locking positioning device on the lower part base and the lower part headrest part.

26. The head coil as claimed in claim 1, further comprising flexible line connections between antenna elements in the lower part headrest part and contacts in the lower part base.

* * * * *